United States Patent
Hutchinson et al.

(10) Patent No.: US 9,849,038 B2
(45) Date of Patent: *Dec. 26, 2017

(54) THERAPY DELIVERY SYSTEMS AND METHODS

(71) Applicant: KCI Licensing, Inc., San Antonio, TX (US)

(72) Inventors: George Hutchinson, San Antonio, TX (US); Richard Paul Mormino, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/574,014

(22) Filed: Dec. 17, 2014

(65) Prior Publication Data
US 2015/0105718 A1    Apr. 16, 2015

Related U.S. Application Data

(60) Continuation of application No. 13/486,493, filed on Jun. 1, 2012, now Pat. No. 8,945,041, which is a
(Continued)

(51) Int. Cl.
*A61F 13/00* (2006.01)
*A61M 1/00* (2006.01)
(Continued)

(52) U.S. Cl.
CPC .... *A61F 13/00068* (2013.01); *A61F 13/0203* (2013.01); *A61F 13/148* (2013.01);
(Continued)

(58) Field of Classification Search
CPC ...... A61F 13/00068; A61F 2013/00536; A61F 13/0203; A61F 13/148; A61M 1/008;
(Continued)

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 A1    3/1986
AU    745271    4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Shefali Patel

(57) ABSTRACT

Fluid removal systems and methods for removing a fluid from a tissue site are presented. The systems include a semi-permeable inbound conduit, which is fluidly coupled to a treatment-fluid delivery unit, for placement proximate to the tissue site, and a semi-permeable outbound conduit, which is fluidly coupled to the inbound conduit and to a treatment-fluid collector, for placement proximate to the tissue site of a patient. The treatment-fluid collector receives a treatment fluid and a recruited fluid from the tissue site. A recruited-fluid determination unit may be coupled to the treatment-fluid collector to determine a volume of the recruited fluid recruited from the patient. The treatment fluid is any fluid (including a gas) that pulls the fluid from an interstitial and intracellular space. A reduced-pressure treatment subsystem may also be included, among other things, for removing ascites and other fluids from a body cavity.

30 Claims, 10 Drawing Sheets

Related U.S. Application Data division of application No. 12/466,973, filed on May 15, 2009, now Pat. No. 8,216,175.

(60) Provisional application No. 61/098,030, filed on Sep. 18, 2008.

(51) Int. Cl.
*A61F 13/02* (2006.01)
*A61F 13/14* (2006.01)
*A61M 27/00* (2006.01)
*A61M 1/28* (2006.01)

(52) U.S. Cl.
CPC .......... *A61M 1/008* (2013.01); *A61M 1/0084* (2013.01); *A61F 2013/00536* (2013.01); *A61M 1/0086* (2014.02); *A61M 1/0088* (2013.01); *A61M 1/285* (2013.01); *A61M 27/00* (2013.01); *A61M 27/002* (2013.01); *A61M 2210/1021* (2013.01); *Y10T 29/49826* (2015.01)

(58) Field of Classification Search
CPC .. A61M 1/0084; A61M 1/0088; A61M 27/00; A61M 27/002; A61M 2027/004; A61M 2210/1017; A61M 2210/1021
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,324,286 A * | 6/1994 | Fowle .................. A61B 18/02 606/20 |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,254,567 B1 * | 7/2001 | Treu .................... A61M 1/1696 604/29 |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,537,241 B1 * | 3/2003 | Odland ............... A61M 1/1678 604/264 |
| 6,553,998 B2 | 4/2003 | Heaton et al. |
| 6,752,794 B2 * | 6/2004 | Lockwood .......... A61M 1/0058 604/313 |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |
| 2009/0048582 A1 * | 2/2009 | Del Bigio ................ A61F 7/12 604/540 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |

(56) References Cited

FOREIGN PATENT DOCUMENTS

| | | |
|---|---|---|
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ð ukie, Ž. Maksimović, Ð . Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

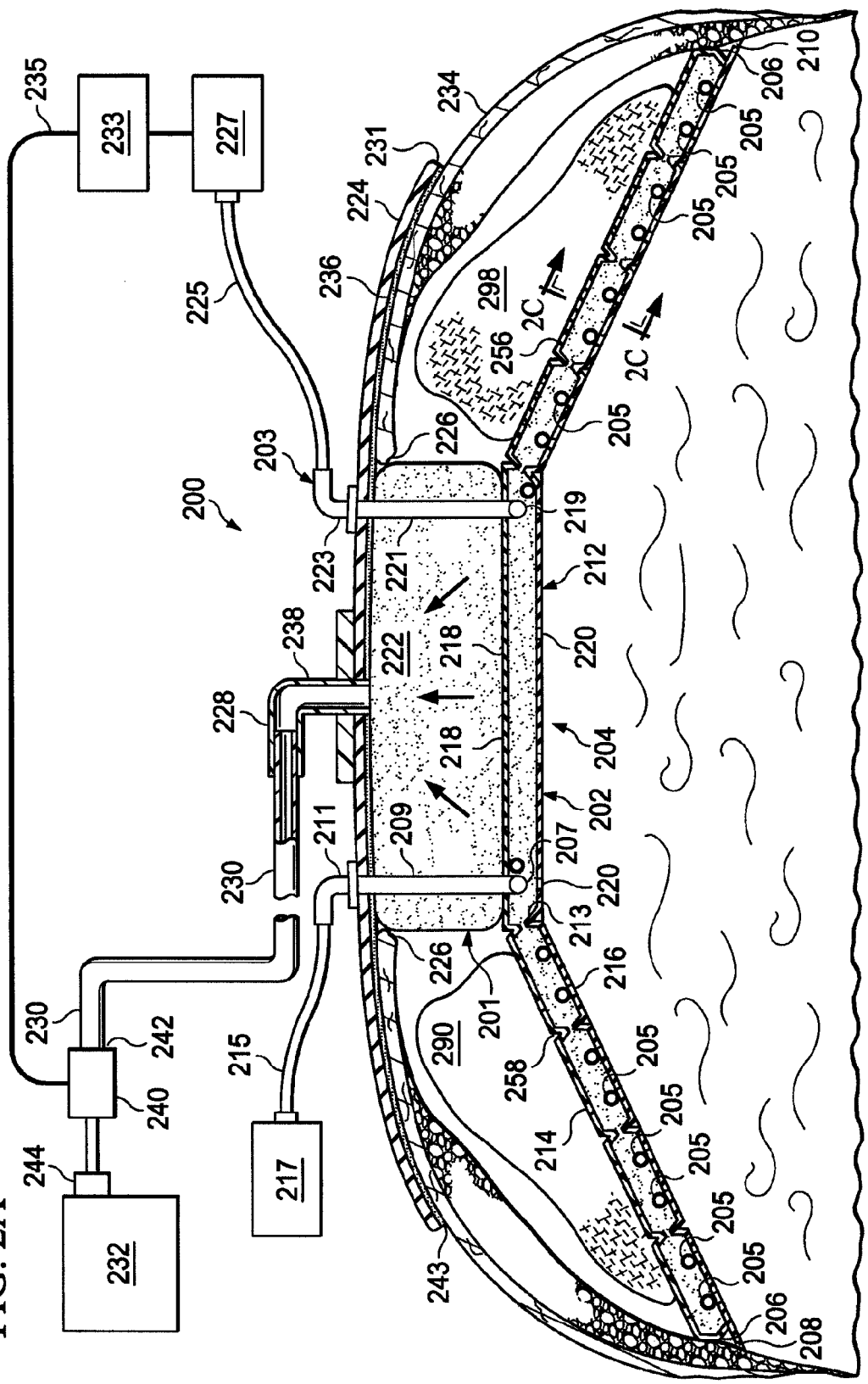

THERAPY DELIVERY SYSTEMS AND METHODS

RELATED APPLICATION

This application is a continuation of U.S. patent application Ser. No. 13/486,493, filed Jun. 1, 2012, which is a divisional of U.S. patent application Ser. No. 12/466,973, filed May 15, 2009, now issued as U.S. Pat. No. 8,216,175 on Jul. 10, 2012, which claims the benefit, under 35 USC §119(e), of the filing of U.S. Provisional Patent Application Ser. No. 61/098,030, entitled "Fluid Removal System and Method," filed Sep. 18, 2008. Each of the above applications is incorporated herein by reference for all purposes.

BACKGROUND

The present invention relates generally to medical treatment systems and, more particularly, to therapy delivery systems and methods.

In certain age brackets, trauma is not an uncommon cause of death. Severe hypovolemia due to hemorrhage is a major factor in many of these deaths. Accordingly, resuscitation of hypovolemic shock remains an important topic. In addressing hypovolemic shock, vigorous restoration of intravascular volume remains the primary task of resuscitation. This task typically requires efforts to control the hemorrhage and to provide fluid resuscitation. Appropriate care of a trauma patient with hemorrhage requires balancing good electrolyte levels, maintaining systemic blood pressure, and minimizing leakage from the microvasculature.

If the initial injury is sufficiently great or the resuscitative efforts are too late or inadequate, the main contributor to damages is the hemodynamic failure itself. If a patient is resuscitated to a degree, however, then inflammatory damage may begin to be the dominant source of damage. In the latter case, the damage may lead to many difficulties and even death.

Among the difficulties, intraabdominal hypertension (IAH) and abdominal compartment syndrome (ACS) may occur as a result of the trauma and also may occur in septic patients. Edema secondary to resuscitation and leaky vasculature may cause the volume of the intraabdominal contents to increase thereby increasing the pressure on all abdominal contents. As the intraabdominal pressure (IAP) increases, perfusion to critical organs may be compromised and may result in multiple organ dysfunction syndrome (MODS) and death. A common technique for diagnosing the possible onset of MODS is by monitoring creatinine and blood urea nitrogen (BUN) levels to detect damage to the kidneys. In avoiding ACS or responding to its onset and in other situations, it may be desirable have a decompressive laparatomy—typically opening the fascia along a midline.

In both resuscitation and steps taken to address intraabdominal pressure, fluid management is important. It would be desirable to have a system and method to help with fluid management. It would be desirable to address fluid removable from the abdominal cavity and to further draw fluids at the interstitial and intracellular level. Furthermore, it would be desirable to have feedback on fluid removal. At the same time, it would be desirable to readily make available reduced-pressure treatment of tissue within the abdominal cavity, which involves the removal of ascites and other fluids.

SUMMARY

Problems with medical treatment systems, devices, and methods are addressed by the systems, apparatus, and methods of the illustrative embodiments described herein. According to one illustrative embodiment, a fluid removal system for removing fluid from a tissue site of a patient includes an inbound conduit for placement proximate to a tissue site on the patient. The inbound conduit is formed from a semi-permeable material. The fluid removal system further includes a treatment-fluid delivery unit that is fluidly coupled to the inbound conduit. The treatment-fluid delivery unit is operable to deliver treatment fluid to the inbound conduit. The fluid removal system further includes an outbound conduit for placement proximate to the tissue site on the patient. The outbound conduit is formed from a semi-permeable material, and the outbound conduit is fluidly coupled to the inbound conduit. The fluid removal system further includes a treatment-fluid collector that is fluidly coupled to the outbound conduit for receiving the treatment fluid and a recruited fluid from the tissue site. A recruited-fluid determination unit may be coupled to the treatment-fluid collector. The recruited-fluid determination unit is operable to determine a volume of fluid recruited from the patient.

According to another illustrative embodiment, a system for providing reduced-pressure treatment within a body cavity of a patient and for removing fluid from water spaces of a tissue site includes a fluid removal subsystem for removing fluids from the water spaces and an open-cavity, reduced-pressure subsystem. The open-cavity, reduced-pressure subsystem includes a treatment device for removing fluids with reduced pressure; a manifold for disposing near the treatment device and operable to distribute reduced pressure to the treatment device; a sealing member for disposing on a portion of the patient's epidermis and operable to form a pneumatic seal over the body cavity; a reduced-pressure delivery conduit; and a reduced-pressure interface for coupling to the sealing member and operable to fluidly couple the reduced-pressure delivery conduit to the manifold. The fluid removal subsystem may include an inbound conduit for placement near to a tissue site on the patient and a treatment-fluid delivery unit fluidly coupled to the inbound conduit. The treatment-fluid delivery unit is operable to deliver treatment fluid to the inbound conduit. The fluid removal subsystem further includes an outbound conduit for placement near to the tissue site on the patient. The inbound conduit and outbound conduit are formed from a semi-permeable material. The outbound conduit is fluidly coupled to the inbound conduit. The fluid removal subsystem further includes a treatment-fluid collector fluidly coupled to the outbound conduit for receiving the treatment fluid and a recruited fluid from the patient's tissue. The fluid removal subsystem may further include a recruited-fluid determination unit coupled to the treatment-fluid collector. The recruited-fluid determination unit is operable to determine a volume of fluid recruited from the patient.

According to another illustrative embodiment, a method of manufacturing a fluid removal system includes the steps of forming an inbound conduit, which is for placement near to a tissue site on the patient, from semi-permeable material and providing a treatment-fluid delivery unit for fluidly coupling to the inbound conduit. The treatment-fluid delivery unit is operable to deliver treatment fluid to the inbound conduit. The method of manufacturing further includes forming an outbound conduit, which is for placement near to the tissue site on the patient, from semi-permeable material and providing a treatment-fluid collector for fluidly coupling to the outbound conduit. The treatment-fluid collector is operable to receive the treatment fluid and a recruited fluid from the patient's tissue. The method of manufacturing may further include providing a recruited-fluid determination unit for coupling to the treatment fluid collecting unit. The recruited-fluid determination unit is operable to determine a volume of fluid recruited from the patient.

According to another illustrative embodiment, a method of removing fluid from a tissue site includes the step of: placing an inbound conduit near to a tissue site on the patient and fluidly coupling a treatment-fluid delivery unit to the inbound conduit. The treatment-fluid delivery unit is operable to deliver a flow of treatment fluid to the inbound conduit. The method of removing fluid from a tissue site further includes placing an outbound conduit near to the tissue site on the patient. The inbound conduit and outbound conduit are formed from a semi-permeable material. The method of removing fluid from a tissue site further includes fluidly coupling the outbound conduit to the inbound conduit; fluidly coupling a treatment-fluid collector to the outbound conduit. The treatment-fluid collector is for receiving the treatment fluid and a recruited fluid from the patient's tissue. The method of removing fluid from a tissue site further includes disposing a treatment fluid within the treatment-fluid delivery unit. The method of removing fluid from a tissue site may also include coupling a recruited-fluid determination unit to the treatment-fluid collector. The recruited-fluid determination unit is operable to determine a volume of fluid recruited from the patient.

The illustrative embodiment of the systems and methods of the present invention may provide a number of perceived advantages. A few examples follow. Technical advantages of the present invention may include that fluids from the tissue water spaces may be removed in a controlled manner. Another advantage is the system may allow for the use of hypertonic solutions to promote intracellular fluid removal without affecting the electrolyte balance. Another advantage is that it may help reduce intraabdominal pressure (IAP) and reduce organ damage. Another advantage is that it may allow for monitoring of the degree of recruited fluid from tissue. Another advantage may be improved safety with respect to hypoperfusion. Another advantage may be that the system and method readily remove ascites and other fluids from the abdominal cavity. Another advantage may be that portions of a system can readily be placed in the paracolic gutters. These are only some non-limiting examples of possible advantages.

Other objects, features, and advantages of the illustrative embodiments will become apparent with reference to the drawings and detailed description that follow.

BRIEF DESCRIPTION OF THE DRAWINGS

FIG. 2A is a schematic diagram, with a portion in cross section, showing another illustrative embodiment of a therapy delivery system;

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein; the description may omit certain information known to those skilled in the art. The following detailed description is, therefore, not to be taken in a limiting sense, and the scope of the illustrative embodiments are defined only by the appended claims.

Figure 1:
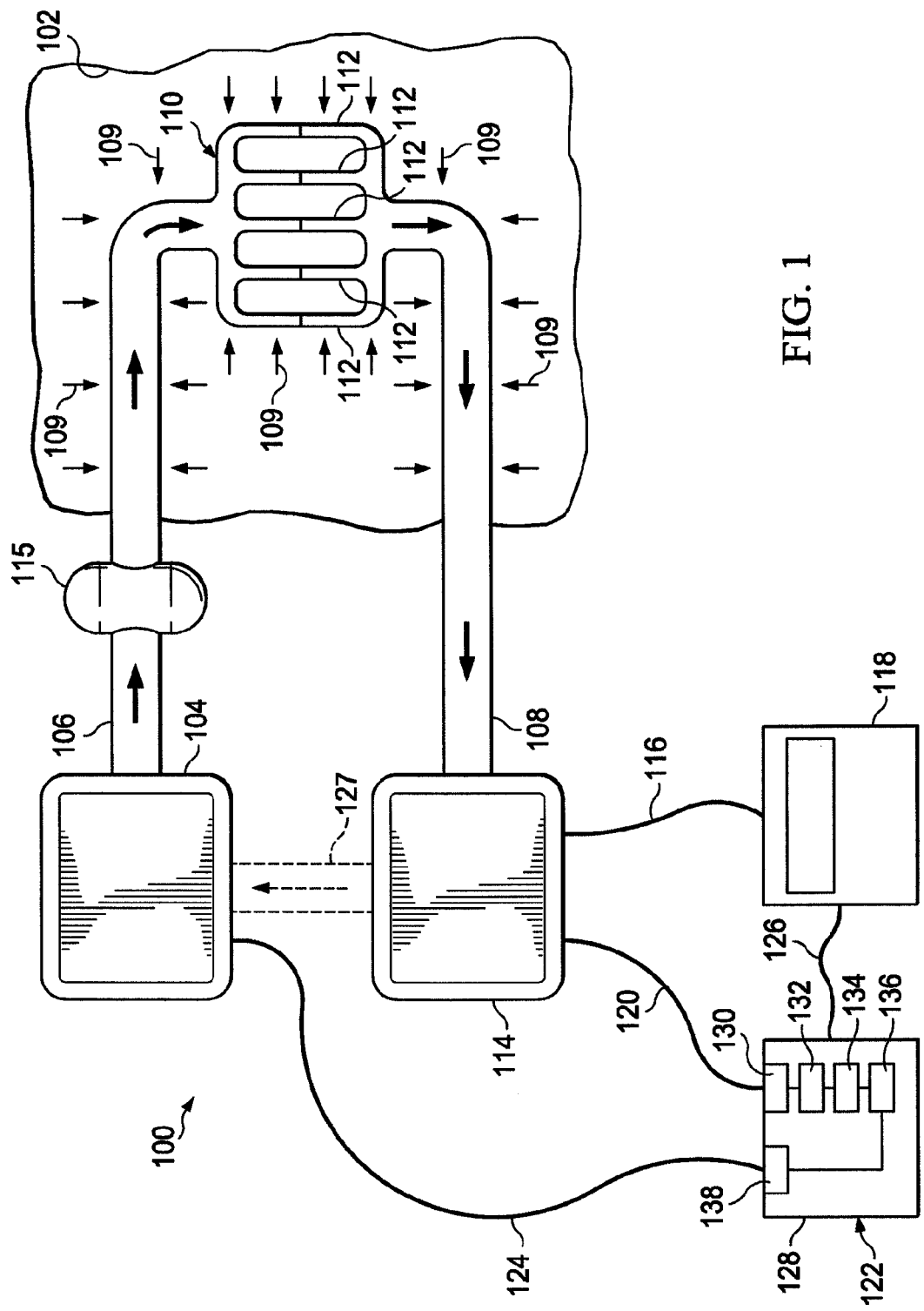
FIG. 1 is a schematic diagram of a therapy delivery system according to one illustrative embodiment.

Referring to FIG. 1, an illustrative embodiment of a therapy delivery system 100 for use in a body cavity, such as an abdominal cavity (see, e.g., cavity opening 226 in FIG. 2A), is presented. In addressing fluid control related to resuscitation, aspects of fluid dynamics, body water spaces (or compartments), and membranes are involved.

There are three body-water spaces: the intravascular volume (plasma volume), which is the volume within the body of vessels; the interstitial volume, which is situated within but not restricted to a particular organ—it is the "in between volume"; and the intracellular volume, which is the volume occurring within cells. As used herein, "water space" means intravascular, interstitial, intracellular, or intercellular volume. Under normal situations, the water volumes in these three spaces have a fairly regular relationship. The interstitial volume is three times the intravascular volume; the intracellular volume is about 2.5 to 3 times the interstitial volume; and the intracellular volume is about 7 to 9 times the intravascular volume. For example, a person of 86 kilograms might have 4 liters of intravascular fluid; 12 liters of interstitial volume; and 36 liters of intracellular fluid. The interstitial volume is in equilibrium with the intravascular volume and acts like a large capacitor that buffers increases or decreases in intravascular volume. The interstitial volume can fluctuate widely, and the interstitial space can greatly expand.

The membranes between water spaces play an important role in the movement of fluids. The intravascular and interstitial spaces are separated by the capillary endothelium, which is a boundary layer that functions differently in various organs. The cell membrane, which obviously addresses the movement between the intracellular volume and interstitial volume, is impervious to proteins, but functions with a sodium-potassium pump that operates at the cell surface to eject sodium from the cells and transport potassium into the cells. The cell membrane is permeable to water. If the sodium-potassium pump shuts down in trauma or for some other reason, passive diffusion of sodium ions into the cells may still occur, increasing the intracellular osmotic pressure. Water will flow down the osmotic gradient, and this may lead to cellular swelling. This may necessitate the removal of fluids.

The characteristics of the membranes allow different approaches to addresses fluid management within the patient, and the therapy delivery system 100 takes advantage of these characteristics. A few illustrative examples that show the characteristics of the membranes follow.

If a balanced salt solution, such as Ringer's lactate solution, is used as a treatment fluid, the fluid dynamics might go as follows. If two liters of this treatment fluid, which is a crystalloid, is added to the intravascular space, after about half an hour, equilibrium is reached. The additional volume of the balanced salt solution is free to cross the capillary endothelium freely and distributes along the lines of the initial fluid distribution of 1:3. So 500 mL (i.e., 2000 mL/4) remains in the intravascular space, and 1500 mL (i.e., 2000 mL*¾) goes on to the interstitial space. There is no movement to the intracellular space because there is no osmotic gradient in this situation.

If the treatment fluid is changed to be a colloid solution, e.g., 5% albumin in saline, then leakage out of the intravascular space is in proportion to the net albumin leakage in the body of about 25 to 35 percent. As such, if two liters of this treatment fluid is infused, approximately 500 mL (i.e., 25%) will leak to the interstitial space and 1500 mL will remain in the intravascular space. Again, there is not an osmotic gradient across the cytosolic membrane of the intracellular space and so there is no movement of volume to the intracellular space.

If the treatment fluid is a hypertonic saline, such as 7.5% saline solution, a considerable retraction of fluid from the intracellular space will be realized. Such a treatment fluid, which may be 7.5% (weight/volume) of sodium chloride, exerts about eight times the normal osmotic pressure of the body on the cells and pulls waters from them very quickly. The pulling of the water is from the intracellular space and not from the interstitial space because the capillary endothelial barrier is freely permeable to small ions such as sodium chloride. So if, 250 mL of such a hypertonic treatment fluid is infused into the intravascular space, it recruits 1750 cc pulled from the intracellular space. So the total volume that is distributed is two L (250 cc added and 1750 pulled from the intracellular space). The total volume is distributed between the intravascular space and the interstitial space according to the ratio of the starting volumes. Thus, if the initial volumes were 4 liters intravascular, 12 liters interstitial, and 36 liters intracellular, then of the two liters of total volume added, the intravascular space would receive approximately 0.5 liters, i.e., (4 L/16 L)*2 L=0.5 L. The interstitial space would receive 1.1 Liters, i.e., (12 L/16 L)*2 L=1.5 L. Great care must be taken, however, with hypertonic treatment fluids since they can cause hypematremia and possibly seizures if given in excessive quantities. The largest volume administered safely under normal conditions is around 250 mL. Still, this approach may be helpful if controlled and the principle helpful in removing intracellular and interstitial fluid as will be described.

Continuing to refer to FIG. 1, the therapy delivery system 100 helps to remove interstitial and intracellular fluid from a tissue site 102, which may include an area within a body cavity. The therapy delivery system 100 will first be described in general terms. A treatment-fluid delivery unit 104 is fluidly coupled to, i.e., in fluid communication with, an inbound conduit 106. The treatment-fluid delivery unit 104 delivers a treatment fluid, which is described elsewhere, into the inbound conduit 106. The inbound conduit 106 is fluidly coupled to an outbound conduit 108. The inbound conduit 106 and outbound 108 may be coupled directly or with a conduit interface 110, which includes a plurality of tributary conduits 112.

Fluid pulled, or recruited, from the interstitial and intracellular space of tissue at the tissue site 102 enters the conduits 106, 112, 108 through their semi-permeable walls. More fluid may be recruited than enters the conduits 106, 112, and 108 and, as explained in connection with FIGS. 2A-D, a reduced-pressure, open-cavity subsystem may be used to remove this additional fluid and any other fluids, e.g., ascites. The interstitial and intracellular fluid being pulled toward the conduits 106, 112, and 108 is represented by arrows 109. The outbound conduit 108 is fluidly coupled to a treatment-fluid collector 114. The treatment fluid and recruited fluid are collected in the treatment-fluid collector 114. The therapy delivery system 100 includes fluid-movement device 115 for moving the treatment fluid through the conduits 106, 108, 112, which can be any means suitable to carry out that function, such as a pump in the treatment-fluid delivery unit 104 that pushes the fluid, a pump in treatment-fluid collector 114 that pulls the fluid, or a pressurized gas that pushes the fluid.

The treatment-fluid collector 114 may include one or more transducers for measuring aspects of the treatment fluid and recruited fluid delivered thereto. For example, the weight of the treatment fluid and recruited fluid may be realized by a transducer, which produces a weight signal, and the weight signal communicated by first coupling means 116 to a communication unit 118, which might be a display. Other transducers might measure temperature, pH, or other attributes of the fluids and produce corresponding transducer signals. The transducer signals may be delivered by a second coupling device 120 to a treatment controller 122. The treatment controller 122 may send and receive signals to and from the treatment-fluid delivery unit 104 by way of third coupling device 124.

The signals may be used for various calculations. For example, if the beginning weight of the treatment fluid is supplied to the treatment controller 122 and the weight of the treatment fluid and recruited fluid are sent to the treatment controller 122 from the transducers in the treatment fluid collector 114, the weight of the recruited fluid can be readily determined. Moreover, if based on programmed protocols, a greater or lesser recruitment rate is desired, a control signal may be sent by the third coupling device 124 to the treatment-fluid delivery unit 104 adjusting the flow rate of the treatment fluid into the inbound conduit 106. Whether directly by the transducer in treatment-fluid collector 114 or by the treatment controller 122 processing signals, the weight or volume of the recruited fluid may be determined, and the transducer in the treatment-fluid collector 114 or the treatment controller 122 that does that may be considered a "recruited-fluid determination unit" As used throughout this document, "or" does not require mutual exclusively. The treatment controller 122 may have its own display or may be coupled by a fourth coupling device 126 to the communication unit 118.

The conduits 106, 108, and 112 are of a semi-permeable membrane material. The conduits 106, 108, and 112 can be made from any material that permits osmosis and is biocompatible. One example is a cellulose acetate material that is hydrophilic, biocompatible, hypoallergenic, pliable, and readily bondable. Furthermore, variables related to the material of the conduits 106, 108, and 112 may be selected to help achieve the desired fluid removal; the variables include pore size and effective diameter. The operating temperature of the treatment fluid will also influence fluid removal. The surface area of the conduits 106, 108, and 112 that is in contact with tissue allows for removal of fluids. The conduits 106, 108, and 112 may be bundled for introduction into the peritoneal cavity and then unbundled. The conduits may be a separate system of conduits as in FIG. 1 or may be associated with a reduced-pressure, open-cavity treatment subsystem as will be explained in connection with FIGS. 2A-2D. The conduits 106 and 108 could be a single, integral conduit.

The inbound conduit 106 and outbound conduit 108 may be connected directly or connected by the tributary conduits 112, which may be a web of smaller connection conduits. The tributary conduits 112 form an arrangement that is analogous in many respects to a capillary in the human body. The tributary conduits 112 help adjust the surface area exposed to the tissue site 102 to achieve a desired fluid removal at the tissue site 102. Typically, a surface is desired that will allow an osmotic gradient to cause flow. The needed area can be determined based on the concentration of the treatment fluid, i.e., the gradient, and the fluid flow rate.

The inbound conduit 106 is fluidly coupled to the treatment-fluid delivery unit 104 (a bus may be used in some other embodiments). The outbound conduit 108 is fluidly coupled to the treatment fluid collector 114 (also a bus may be used in some other embodiments). The conduits 106 and 108 may be coupled to the treatment-fluid delivery unit 104 and treatment fluid collector 104 respectively by any manner; for example, the coupling may be accomplished by epoxy or any fixing agent, welding, an interference connection, heat sealing, electrocautery, etc. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid is in communication between the designated parts or locations.

The treatment fluid introduced by the treatment-fluid delivery unit 104 into inbound conduit 106 may be any of numerous fluids or gases. The treatment fluid may be any fluid that recruits fluid from the adjacent or neighboring tissue at tissue site 102 and in particular from the intracellular space. This would usually occur by using a hyperosmotic fluid. The treatment fluid may be for example, a hypertonic solution of hygroscopic material or a dry gas. In one embodiment, a 7.5% (weight/volume) of sodium chloride solution may be used as referenced earlier. Other hyperosmotic solutions may be used, such as a sodium chloride and dextran (e.g., Macrodex® solution from Pharmacia Fine Chemicals, Piscataway, N.J., in deionized, sterile water). Other illustrative examples of the treatment fluid include CaCl2, KCl, NaCl, or Dextran solutions. Still other examples include hyperosmotic/hyperoncotic solution (1.2M NaCl, 6% Dextran-70), a hyperosmotic sodium chloride solution (1.2M), or a hyperoncotic Dextran-70 solution 6%.

The treatment fluid might also be a dried gas that is passed in the conduits 104, 106, 112. As the gas passes through the inbound conduit 106, fluid from neighboring tissue diffuses through the conduit 106 and evaporates into the flowing gas of the treatment fluid. The gas is chosen and situated to maximize the partial pressure gradient between the surface of the conduits 104, 106, 112, where the surface is saturated, and the flowing stream of treatment fluid, while at the same time minimizing heat loss to the patient. The heat loss can be addressed by using a gas warmer at the treatment-fluid delivery unit 104. Again, numerous gases might be used, e.g., $CO_2$, nitrogen, air, etc.

The flow rate of the treatment fluid may be controlled by the fluid-movement device 115. The flow rate may be adjusted to account for the length of conduits 106, 108, 112 actually deployed in the body cavity near tissue site 102, the temperature of the operating environment, or the rate at which fluid removal is desired. To monitor fluid removal, the treatment fluid is collected at the treatment-fluid collector 114 and analyzed to determine the amount of additional fluid, or recruited fluid, supplied from the patient's body. In one embodiment, a simple scale is used to determine the weight of the outbound fluid which is compared to the weight of the inbound treatment fluid to compute the weight of the recruited fluid, i.e., the difference. The difference is then displayed for the healthcare provider on communication unit 118.

The difference may be used digitally by the treatment controller 122 to automatically make adjustments as previously suggested. The removed fluid's (treatment fluid and recruited fluid) characteristics can be used in a feedback loop by the treatment controller 122 to automatically adjust the inbound treatment fluid in terms of flow rate, temperature, or other variables to control the amount of fluid recruited. If the treatment fluid is a gas, the gas can be passed through a condenser to remove the fluid for quantification and possible recycle of the gas as the treatment fluid. The recycled gas may optionally be returned by return conduit 127.

The treatment controller 122 includes a housing unit 128, which contains various components for analyzing data on the treatment fluid and recruited fluid and controlling treatment-fluid delivery unit 104. The treatment controller 122 may receive a number of different input signals from input means, such as transducer signals delivered by the second coupling device 120 from the treatment fluid collector 114. The treatment controller 122 is shown with an input device 130. If the signal delivered to input device 130 is not already in a digitized form, an analog-to-digital converter 132 may be included. The signals received in the input device 130 may be then delivered to a buffer memory and either supplied to a memory unit or device 134 or directly delivered to a microprocessor 136. It may be desirable to keep a recording of the input data to allow different determinations.

The microprocessor 136 is operable to carry out a number of different determinations and may have a number of outputs. An output device 138 may deliver one or more output signals to the third coupling device 124; for example, a control signal may be delivered to the treatment-fluid delivery unit 104 and on to the fluid-movement device 115 to control the flow rate therein. As another example, the treatment controller 122 may monitor the temperature of the fluid delivered through the outbound conduit 108 and determine that more or less heat is needed, and a temperature control signal might be sent by the treatment controller 122 via the third coupling device 124 to the treatment-fluid delivery unit 104 that may include a heating element for heating the treatment fluid. The treatment controller 122 is shown in one illustrative embodiment utilizing a microprocessor, but it is to be understood that many other approaches might be used.

In operation, the treatment-fluid delivery unit 104 delivers and causes the treatment fluid to flow through the conduits 106, 108, and 112, and to the treatment fluid collector 114. As the treatment fluid moves through the conduits 106, 108, 112, an osmotic imbalance occurs between the treatment fluid and the neighboring tissue of the tissue site 102. In order to seek equilibrium, water seeks to flow from the tissue to the inside of the conduits 106, 108, 112 in an effort to achieve the same concentration of saline in the tissue as in the treatment fluid. Because of the difference in volume between the treatment fluid and the fluid in the tissue of the body, however, no practical change in the saline concentration in the tissue results. The tissue of the body will deliver fluid from the intracellular space and the interstitial space toward and into the conduits 106, 108, 112. The fluid will be delivered from the intracellular space at approximately a 3:1 ratio relative to the interstitial space.

While the treatment fluid travels through the conduits 106, 108, 112, there is a concentration gradient between the tissue and the conduits. In this situation, nature tries to balance the concentrations, but because the relatively larger molecules of the treatment fluid cannot leak into the tissue (interstitial and intracellular spaces) to restore balance, the smaller molecules, e.g., water, move into the conduits 106, 108, 112 and their vicinity. The water goes from the intracellular space and interstitial space into the conduits 106, 108, 112 and their vicinity. Water that is not pulled through the semi-permeable walls of the conduits 106, 108, 112 may be collected and removed if possible by another means. This latter comments leads to the next embodiment that includes an open-cavity, reduced-pressure subsystem that helps remove water.

Referring to FIG. 2A-2D, an illustrative embodiment of a system 200 for fluid removal and reduced-pressure treatment is presented. The system 200 removes fluids from the interstitial and intracellular spaces of a tissue site 204 by way of a fluid removal subsystem 203 and removes ascites and other fluids from the abdominal cavity using an open-cavity, reduced-pressure subsystem 201. The system 200 includes a treatment device 202. The treatment device 202 is typically placed within the patient's abdominal cavity. The open-cavity, reduced-pressure subsystem 201 and the treatment device 202 remove fluids, e.g., ascites, and also allows general reduced-pressure treatment of tissue at or near the tissue site 204 within the abdominal cavity.

The treatment device 202 is disposed within a cavity of the patient to treat a wound or given area or generally tissue at or near the tissue site 204. The treatment device 202 includes a plurality of encapsulated leg members 206. One or more of the plurality of encapsulated leg members 206 may be placed in or near a first paracolic gutter 208, and one or more of the plurality of encapsulated leg members 206 may be placed in or near a second paracolic gutter 210. Each of the plurality of encapsulated leg members 206 is coupled to a central connection member 212, and there is fluid communication between the plurality of encapsulated leg members 206 and the central connection member 212. Both the plurality of encapsulated leg members 206 and the central connection member 212 are formed with fenestrations 214, 216, 218, 220 that allow fluids in the cavity to pass through the fenestrations 214, 216, 218, and 220. The plurality of encapsulated leg members 206 may be arranged about the central connection member 212 in a manner analogous to encapsulated leg members 312 in FIG. 3 as discussed further below.

A manifold 222, or manifold pad, distributes reduced pressure to the treatment device 202. A sealing member 224 provides a pneumatic seal over a cavity opening 226. One or more skin closure devices may be placed on the epidermis 234, or skin. Reduced pressure is delivered to the manifold 222 through a reduced-pressure interface 228, which is coupled to a reduced-pressure delivery conduit 230. A reduced-pressure source 232 delivers reduced pressure to the reduced-pressure conduit 230.

The tissue site 204 may be the bodily tissue of any human, animal, or other organism. In this embodiment, the tissue site 204 is generally tissue in the abdominal cavity. Typically a patient's abdominal contents function as the support for the treatment device 202.

Reduced pressure may be applied to the tissue site 204 to help promote removal of ascites, exudates or other liquids from the tissue site as well as, in some situations, to stimulate the growth of additional tissue. As used herein, the "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Unless otherwise indicated, values of pressure stated herein are gauge pressures.

The manifold 222, or manifold pad, is placed proximate, or near, the central connection member 212. The manifold 222 may take many forms. The term "manifold" as used herein generally refers to a substance or structure that is provided to assist in applying reduced pressure to, delivering fluids to, or removing fluids from a tissue site. The manifold 222 typically includes a plurality of flow channels or pathways that are interconnected to improve distribution of fluids provided to and removed from tissue (or devices) around the manifold 222. The manifold 222 may be a biocompatible material that is capable of being placed in contact with tissue or proximate tissue and distributing reduced pressure to the tissue site (or devices). Examples of manifolds may include without limitation devices that have structural elements arranged to form flow channels, cellular foam such as open-cell foam, porous tissue collections, and liquids, gels and foams that include or cure to include flow channels. The manifold 222 may be porous and may be made from foam, gauze, felted mat, or any other material suited to a particular biological application. In one embodiment, the manifold 222 is porous foam and includes a plurality of interconnected cells or pores that act as flow channels. The porous foam may be polyurethane, open-cell, reticulated foam, such as a GranuFoam® material manufactured by Kinetic Concepts, Incorporated of San Antonio, Tex. Other embodiments may include "closed cells." Other layers may be included in or on the manifold 222, such as absorptive materials, wicking material, hydrophobic materials and hydrophilic materials.

The sealing member 224 is placed over the abdominal cavity opening 226 and provides a pneumatic seal adequate for the open-cavity, reduced-pressure subsystem 201 to hold reduced pressure at the tissue site 204. The sealing member 224 may be a cover that is used to secure the manifold 222 on the central connection member 212. While the sealing member 224 may be impermeable or semi-permeable, the sealing member 224 is capable of maintaining reduced pressure at the tissue site 204 after installation of the sealing member 224 over the abdominal cavity opening 226. The sealing member 224 may be a flexible over-drape or film formed from a silicone-based compound, acrylic, hydrogel or hydrogel-forming material, or any other biocompatible material that includes the impermeability or permeability characteristics desired for a tissue site or other application.

The sealing member 224 may further include an attachment device 243 to secure the sealing member 224 to a patient's epidermis 234. The attachment device 243 may take many forms; for example, an adhesive layer 236 may be positioned along a perimeter of the sealing member 224 or any portion of the sealing member 224 to provide the seal. The adhesive layer 236 might also be pre-applied and covered with a release member that is removed at the time of application.

The reduced-pressure interface 228 may be, as one example, a port or connector 238, which permits the passage of fluid from the manifold 222 to the reduced-pressure delivery conduit 230 and reduced pressure from the reduced-pressure delivery conduit 230 to the manifold 222. For example, ascites collected from the tissue site 204 using the manifold 222 and the treatment device 202 may enter the reduced-pressure delivery conduit 230 via the connector 238. In another embodiment, the system 200 may omit the connector and the reduced-pressure delivery member 230 may be inserted directly into the sealing member 224 and into the manifold 222. The reduced-pressure delivery conduit 230 may be a medical conduit or tubing or any other means for transportation a reduced pressure.

Reduced pressure is generated and supplied to the reduced-pressure delivery conduit 230 by the reduced-pressure source 232. A wide range of reduced pressures may be developed as both constant and varying pressures; the range may be −50 mm Hg to −400 mm Hg and more typically −100 mm Hg to −250 mm Hg. The range would usually include −200 mm Hg. A number of different devices, such as representative device 240, might be added to a medial portion 242 of the reduced-pressure delivery conduit 230. For example, a fluid reservoir, or collection member, might be added to hold ascites, exudates, and other fluids removed. Other examples of representative devices 240 that may be included on the medial portion 242 of the delivery conduit 230 include a pressure-feedback device, volume detection system, blood detection system, infection monitoring system, flow monitoring system, temperature monitoring system, etc. Some of these devices, e.g., the fluid collection member, may be formed integral to the reduce-pressure source 232. For example, a reduced-pressure port 244 on the reduced-pressure source 232 may include a filter member that includes one or more filters and may include a hydrophobic filter that prevents liquid from entering an interior space.

Figure 2B:
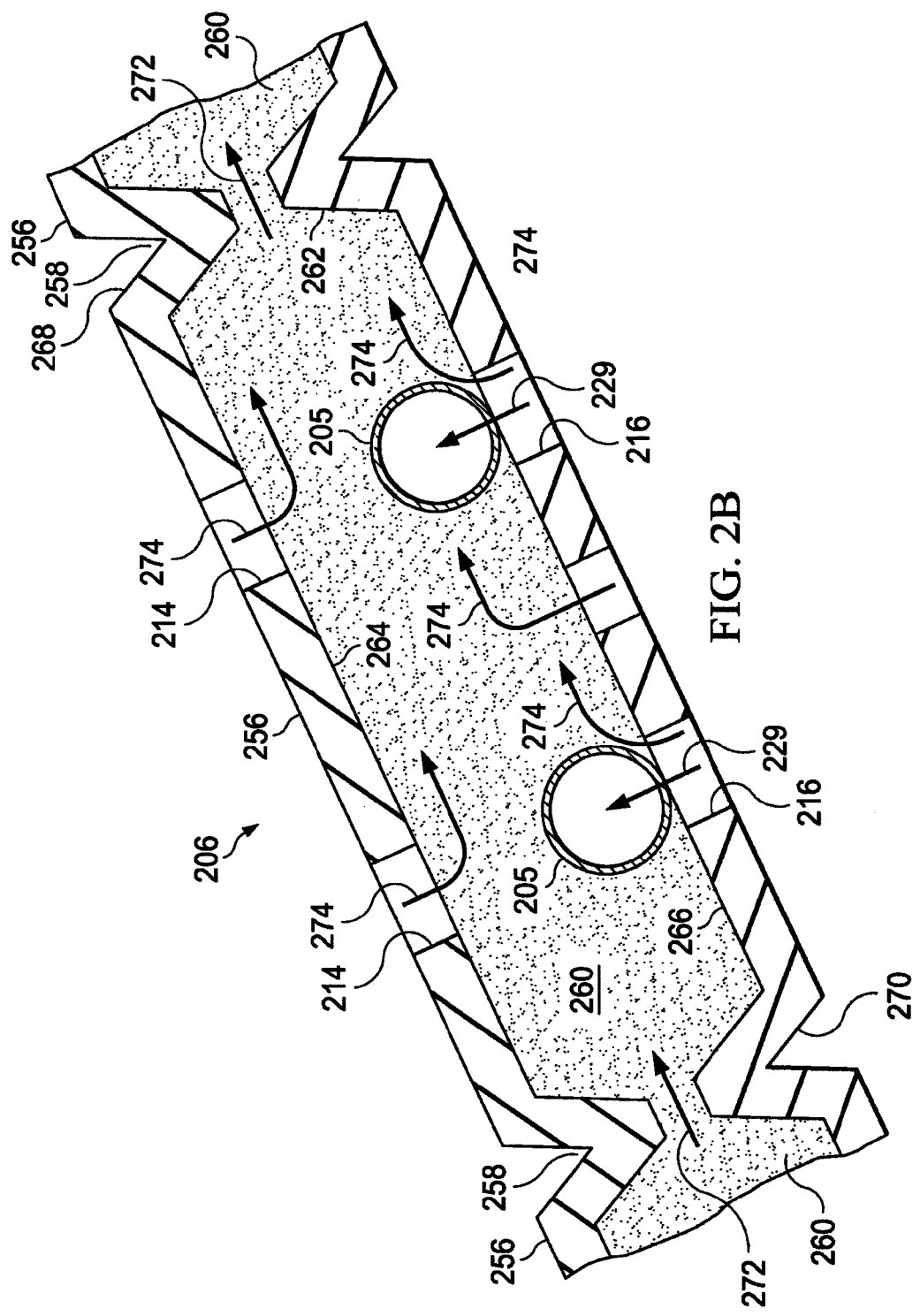
FIG. 2B is a schematic cross section of a detail of the therapy delivery system of FIG. 2A.

Referring primarily to FIG. 2B, a schematic, longitudinal cross section of a leg module 256 of an encapsulated leg member 206 is presented. Each encapsulated leg member 206 may be formed with a plurality of leg modules 256. Each leg module 256 has a leg manifold member 260, which may be a single manifold member that runs between the leg modules 256 or may be discrete components of a manifold material in each leg module 256 that make up the leg manifold member 260 of the encapsulated leg member 206. The leg manifold member 260 is disposed within an interior portion 262 of the encapsulated leg member 206. The leg manifold member 260 has a first side 264 and a second, patient-facing side 266. A first leg encapsulating member 268, which is formed with fenestrations 214, is disposed on the first side 264 of the leg manifold member 260. Similarly, a second leg encapsulating member 270, which has fenestrations 216, is disposed on the second, patient-facing side 266 of leg manifold member 260. The second leg encapsulating member 270 may be a portion of a non-adherent drape, such as non-adherent drape 302 in FIG. 3. As shown in the longitudinal cross section of FIG. 2B by arrows 272, fluid may flow between adjacent leg modules 256. As shown by arrows 274, fluid is able to enter fenestrations 214 and 216 and flow into the leg manifold member 260 and then flow, as represented by flow arrows 272, toward the central connection member 212.

Figure 2C:
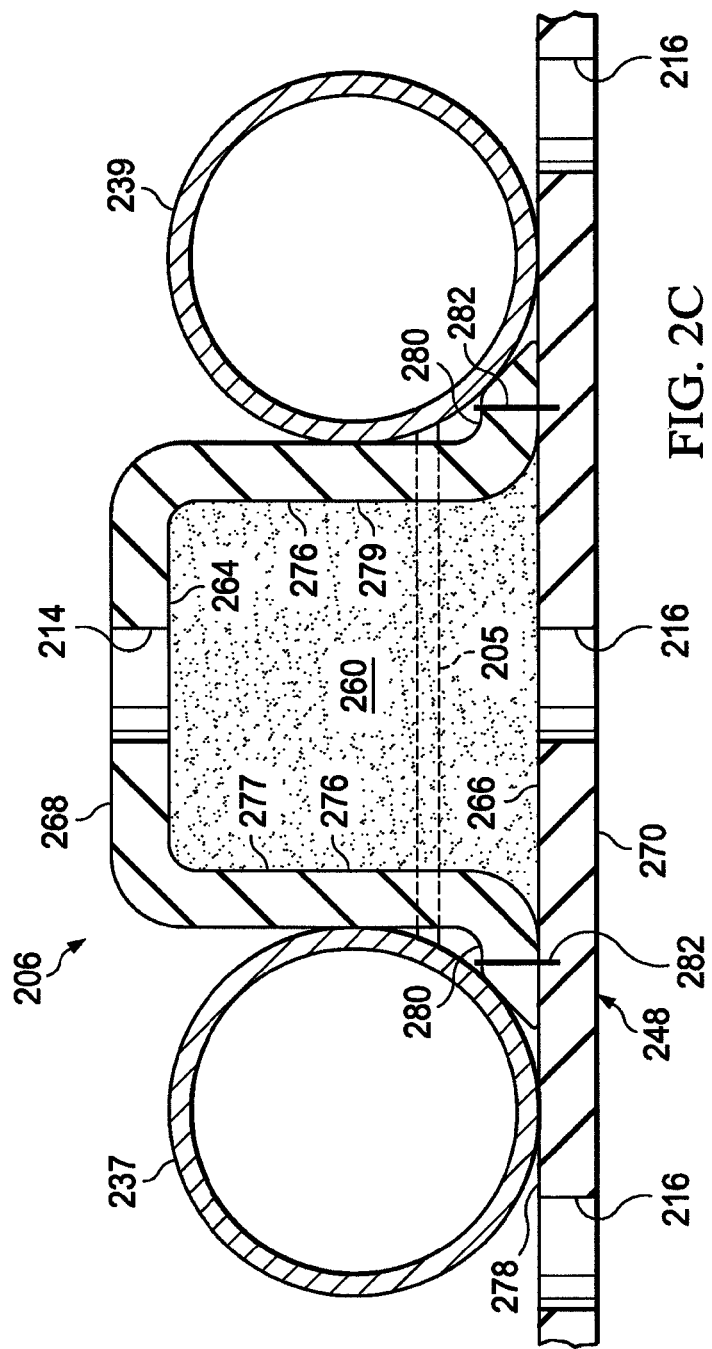
FIG. 2C is a schematic cross section of a portion of the therapy delivery system shown in FIG. 2A taken along line 2C-2C.

Referring now to FIG. 2C, a lateral cross section of a portion of encapsulated leg member 206 is presented. As before, it can be seen that the first side 264 of the leg manifold member 260 is covered with the first leg encapsulating member 268 and that the second, patient-facing side 266 of the leg manifold member 260 is covered by the second leg encapsulating member 270, which in this instance is a portion of a non-adherent drape 248. In this illustrative embodiment, the peripheral edges 276 of the leg manifold member 260 are also covered by a portion of the first leg encapsulating member 268. The peripheral edges 276 include a first lateral edge 277 and a second lateral edge 279. The first leg encapsulating member 268 surrounds the first side 264 and the peripheral edges 276 and extends down onto a first surface 278 of the non-adherent drape 248 and forms extensions 280. The extensions 280 are coupled to the second leg encapsulating member 270 by welds 282. The first leg encapsulating member 268 may be coupled to the second leg encapsulating member 270 using any known technique, including ultrasonic welding, RF welding, bonding, adhesives, cements, etc.

Figure 2D:
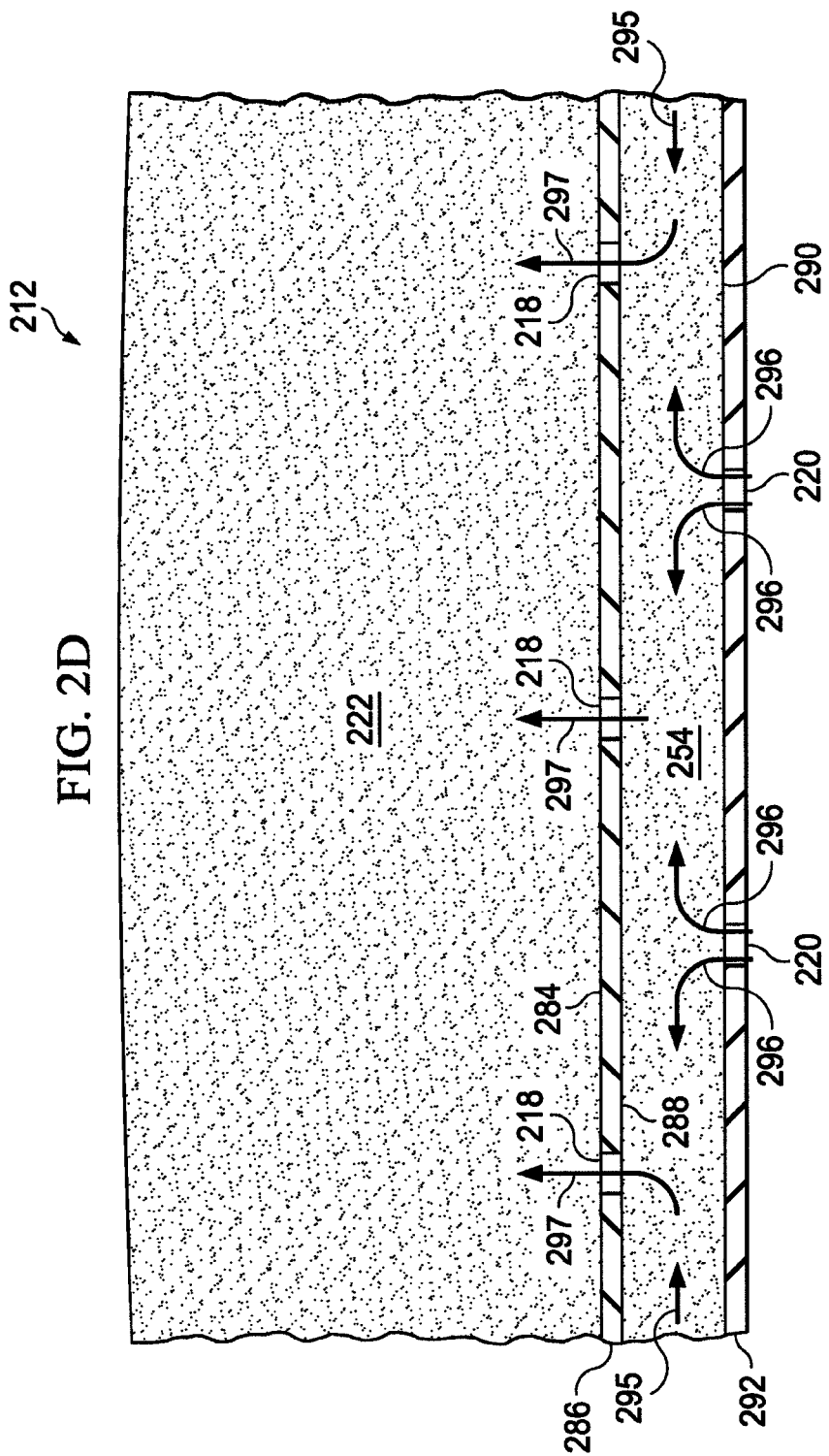
FIG. 2D is a schematic cross section of a portion of the therapy delivery system shown in FIG. 2A.

Referring now to FIG. 2D, a schematic cross section of a portion of the central connection member 212 is presented. The central connection member 212 is formed with a connection manifold member 254 that is encapsulated with a first connection encapsulation member 286, which has fenestrations 218. The first connection encapsulation member 286 is disposed on a first side 288 of the connection manifold member 254. A second, patient-facing side 290 of the connection manifold member 254 has a second connection encapsulation member 292 disposed proximate the connection manifold member 254. The second connection encapsulation member 292 is formed with fenestrations 220. The first connection encapsulation member 286 has a peripheral edge (not explicitly shown), which is analogous to the peripheral edge 311 of the central connection 310 in FIG. 3. In a similar fashion, the second connection encapsulation member 292 has a peripheral portion that lines up with the peripheral edge of the first connection encapsulation member 286. The peripheral edge of the first connection encapsulation member 286 is coupled to the peripheral portion of the second connection encapsulation member 292, except at the leg coupling areas 252 in order to provide flow channels for fluid within the encapsulated leg member 206 to flow into the connection manifold member 254 as suggested by reference arrows 295 in FIG. 2D.

Fluid may also enter directly into the connection manifold member 254 by flowing through fenestrations 220 as suggested by arrows 296. The manifold 222 is disposed proximate to the first connection encapsulation member 286, and when reduced pressure is applied to the manifold 222, the reduced pressure causes fluid to flow from the connection manifold member 254 through fenestrations 218 and into the manifold 222 as is suggested by arrows 297. The fluid continues to flow in the direction of the reduced-pressure interface 228 through which the fluid is delivered to the reduced-pressure delivery conduit 230.

Referring to FIGS. 2A-D, the operation of the open-cavity, reduced-pressure subsystem 201 will be presented. The open-cavity, reduced-pressure subsystem 201 may be used by first sizing the treatment device 202 as will be explained further below in connection with FIG. 3A. The non-adherent drape 248 with the plurality of encapsulated leg members 206 is placed within the abdominal cavity and both the non-adherent drape 248 and the plurality of encapsulated leg members 206 are distributed on the abdominal contents; this may include placing at least one encapsulated leg member 206 down in or near the paracolic gutters 208 and 210. The manifold 222 is placed down adjacent to the first side 284 of the first connection encapsulation member 286 (see FIG. 2D). The sealing member 224 may then be applied over the abdominal cavity opening 226 to provide a pneumatic seal over the abdominal cavity opening 226 and to help hold the abdominal cavity opening 226 closed. In addition to applying the sealing member 224, the abdominal opening 226 may be further closed or reinforced using mechanical closing means or using a reduced-pressure closure system.

Application of the sealing member 224 may be accomplished in a number of ways, but according to one illustrative embodiment, releasable backing members that are on the adhesive layer 236 of the sealing member 224 are removed and then the sealing member 224 is placed against the patient's epidermis 234 about the abdominal opening 226. The reduced-pressure interface 228, such as port 238, is then attached to the sealing member 224 such that reduced pressure can be delivered to the port 238 through the sealing member 224 and provided to the manifold 222. The reduced-pressure delivery conduit 230 is fluidly coupled to the reduced-pressure interface 228 and to the reduced-pressure port 244 on the reduced-pressure source 232.

The reduced-pressure source 232 is activated providing reduced pressure into the reduced-pressure delivery conduit 230, which delivers reduced pressure to the reduced-pressure interface 228 and into the manifold 222. As shown in FIG. 2D, the manifold 222 distributes the reduced pressure and draws fluid through the fenestrations 218 from the connection manifold member 254. The connection manifold member 254 draws fluids from the abdominal cavity through fenestrations 220 and pulls fluid from the plurality of encapsulated leg members 206 as suggested by flows arrows 295. Referring primarily to FIG. 2B, the fluid flows into the encapsulated leg member 206 through the fenestrations 214 on the first leg encapsulating member 268 and through the fenestrations 216 on the second leg encapsulating member 270. The fluid flows through the encapsulated leg member 206 towards the connection manifold member 254 as suggested by arrow 272.

The fluid-removal subsystem 203 and its operation will now be described. In a manner analogous to the inbound conduit 106 and outbound conduit 108 of FIG. 1 and the plurality of inbound conduits 326 and outbound conduits 334 of FIG. 3 described below, a plurality of inbound conduits, e.g., inbound conduit 237 (FIG. 2C), and a plurality of outbound conduits, e.g., outbound conduit 239 (FIG. 2C), go along each encapsulated leg member 206 and are fluidly coupled by a plurality of tributary conduits 205 (see FIGS. 2B and 2C).

The inbound conduits 237 are fluidly coupled to a treatment-fluid delivery bus 207 (see FIG. 2A), which is fluidly coupled to a first connecting conduit 209. The first connecting conduit 209 is fluidly coupled to a first interface 211, which may be an elbow port as shown. A treatment-fluid delivery conduit 215 is fluidly coupled to the first interface 211 and to a treatment-fluid delivery source 217. A treatment-fluid delivery unit (see by analogy treatment-fluid delivery unit 104 in FIG. 1) functions to deliver a flow of treatment fluid to the plurality of inbound conduits 237, and in the illustrative embodiment of FIG. 2A, the treatment-fluid delivery unit may include the treatment-fluid delivery source 217, the treatment-fluid conduit 215, the first interface 211, the first connecting conduit 209, and the treatment-fluid delivery bus 207.

The outbound conduits 239 are fluidly coupled to a treatment-fluid collecting bus 219 (see FIG. 2A), which is fluidly coupled to a second connecting conduit 221. The second connecting conduit 221 is fluidly coupled to a second interface 223, which may be an elbow port as shown. The second interface 223 is fluidly coupled to a recovered-fluid conduit 225, which is also fluidly coupled to a treatment-fluid receptacle 227, which receives the returning treatment fluid and any recruited fluids from the tissue site 204. The treatment-fluid receptacle 227 may include transducers to determine the weight or volume of the recovered fluid (i.e., all the fluid) and the weight or volume of the recruited fluid (i.e., from the interstitial and intracellular space). The treatment-fluid receptacle 227 may also include transducers for other data, such as temperature data. As with the treatment-fluid collector 114 in FIG. 1, the treatment-fluid receptacle 227 may have a communication unit and a treatment controller 233 associated with treatment-fluid receptacle 227. A treatment-fluid collecting unit (see by analogy treatment-fluid collector 114 in FIG. 1) functions to receive the returning treatment fluid and recruited fluid, and the illustrative embodiment of FIG. 2A, the treatment-fluid collecting unit includes the treatment fluid collecting bus 219, the second connecting conduit 221, the second interface 223, the recovered-fluid conduit 225, and the treatment-fluid receptacle 227.

As treatment fluid travels through the inbound conduits 237, the outbound conduits 239, and the tributary conduits 205, fluid is recruited from the interstitial and intracellular spaces of the tissue at or near the tissue site 204—generally referenced as "tissue site." The recruited fluid, or at least some of the recruited fluid, will enter the conduits 237, 239, 205, such as is suggested by arrows 229 in FIG. 2B. At the same time, some of the recruited fluid will leave the interstitial and intracellular space but before entering the conduits 237, 239, 205, will be pulled into the apertures 114 and 116 and into leg manifold member 260 as suggested by arrows 274 in FIG. 2B. The open-cavity, reduced-pressure subsystem 201 will pull that recruited fluid, ascites, exudates, and any other fluids to the reduced-pressure source 132. It should be noted that the representative device 240 may be a canister for holding the fluid delivered thereto and may further include one or more transducers or means for determining the weight and volume of the fluid delivered thereto and that information may be reported by the coupling device 235 to the treatment controller 233 to allow the recovered fluid from the open-cavity, reduced-pressure subsystem 201 to be factored into the fluid management situation.

Referring to FIG. 2C, the inbound conduit 237 may be coupled to the encapsulated leg 206 by the tributary conduits 205 running through the encapsulated leg member 206 or by adhesive, or welding, or any other means. The fenestrations 216 may be arranged to be dense and near to the conduits 237 and 239 to facilitate interaction of the treatment fluid in the conduits 237 and 239 with the tissue site 204. In another approach, the treatment device 202 could be flipped so that the drape and first side of the first leg encapsulating member 268 is against the patient and the conduits 237 and 239 would be directly against the tissue.

The illustrative fluid-removal systems 100 and 300 and fluid-removal subsystem 203 presented herein are typically introduced through an open cavity, but other ways are possible. For example, the fluid-removal systems 100 and 300 and fluid-removal subsystem 203 may be introduced laprascopically into the patient. In such a situation, the conduits are introduced with a string of pressure manifolding devices, such as the plurality of encapsulated leg members 206 (FIG. 2A), with the laparoscope, and then the inbound conduits 237 and outward conduits 239 are fluidly coupled to a treatment-fluid delivery bus, e.g., bus 324 in FIG. 3, and a treatment-fluid collecting bus, e.g., 330 in FIG. 3, respectively external to the patient. This also points out that in some situations the buses 324 and 330 may be located at a site external to the patient.

Figure 3:
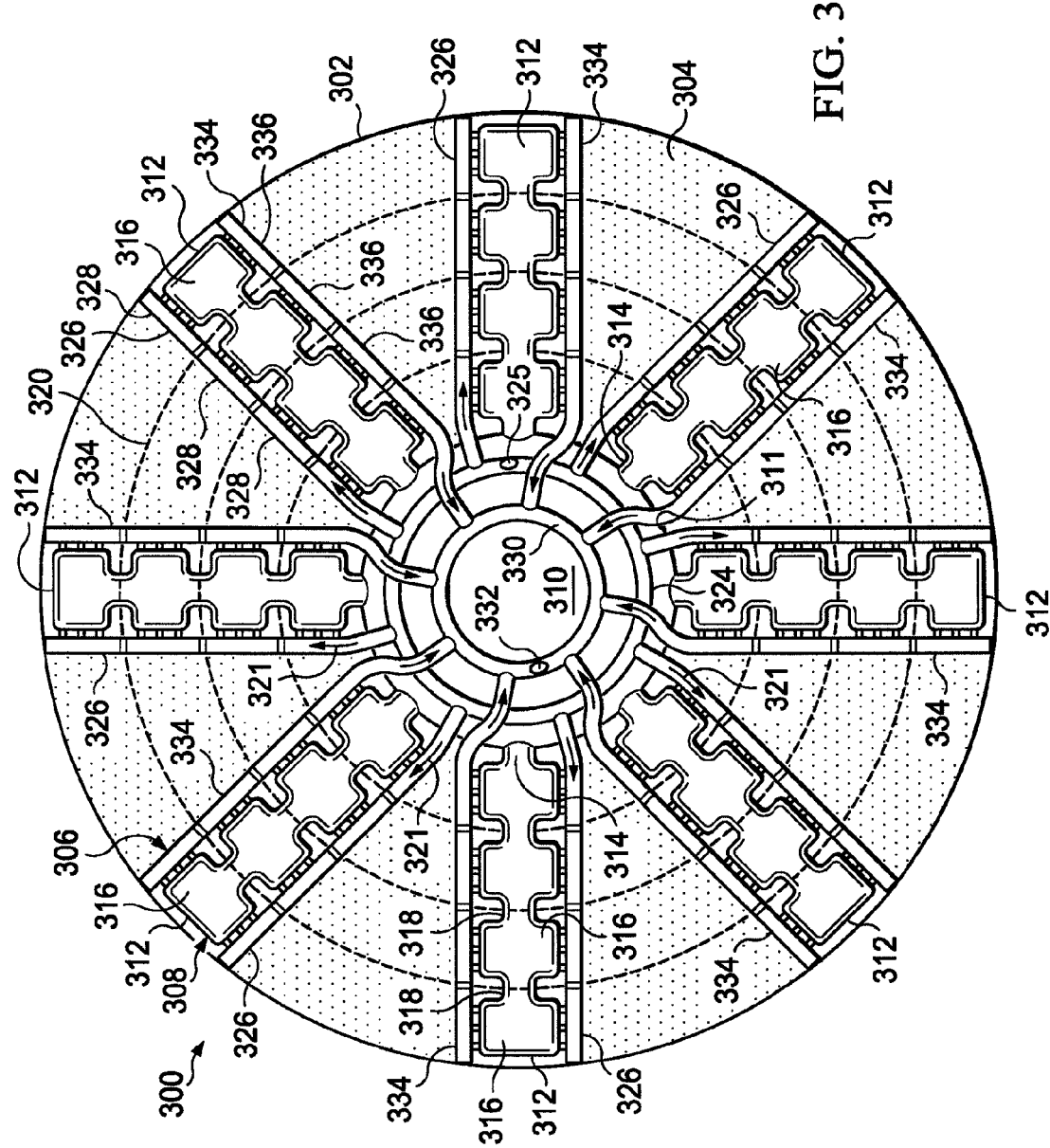
FIG. 3 is a schematic plan view of another illustrative embodiment of a therapy delivery system.
Figure 4:
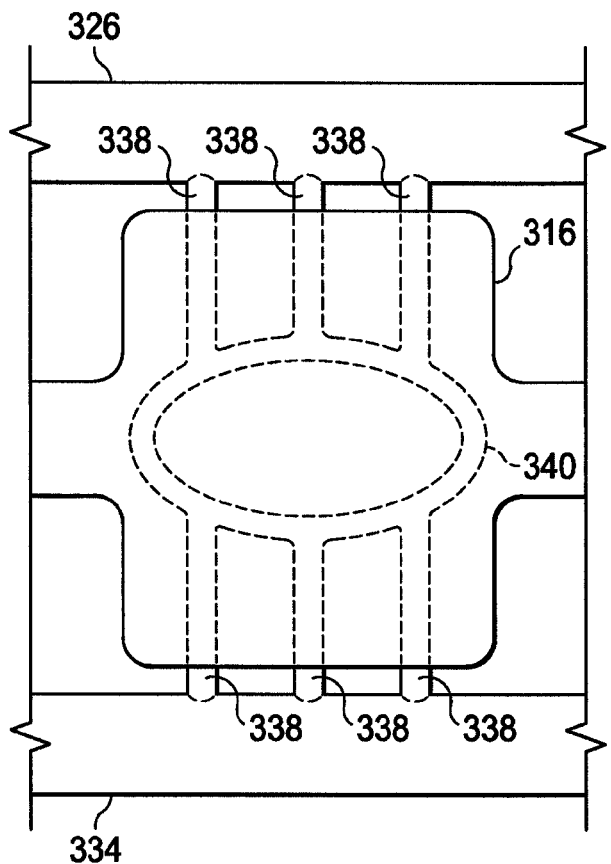
FIG. 4 is a schematic plan view of a detail of a portion of the therapy delivery system of FIG. 3.
Figure 5:
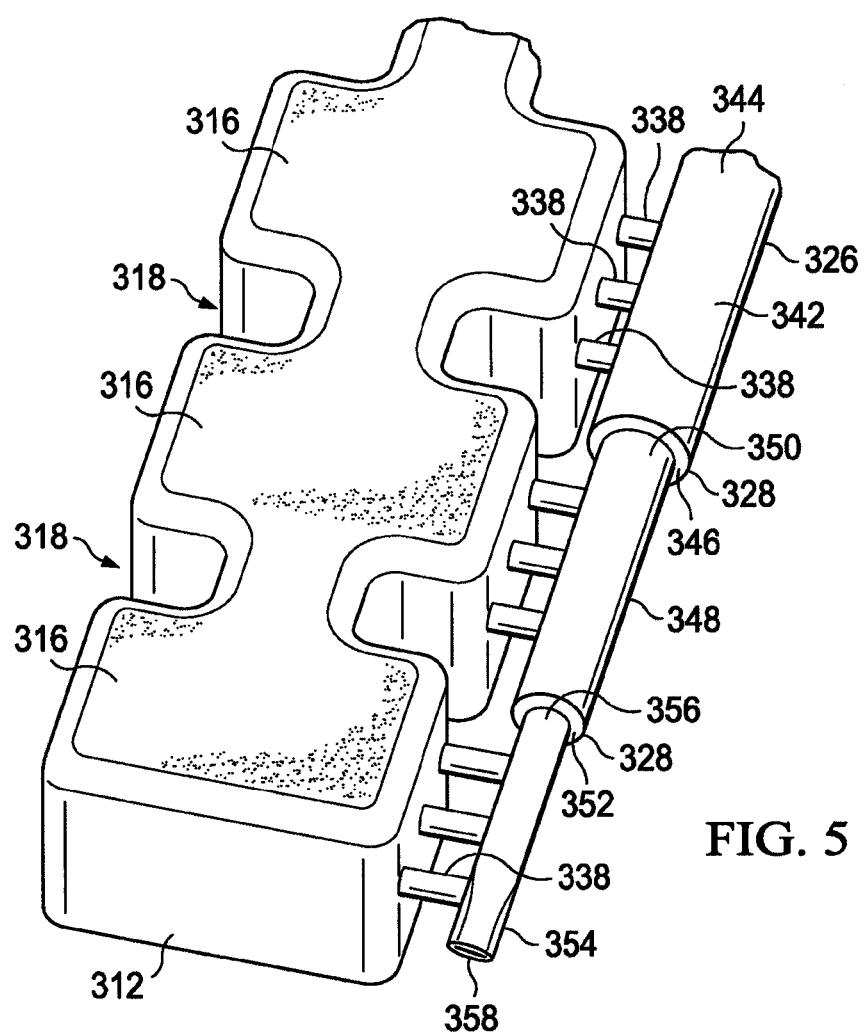
FIG. 5 is a schematic, perspective view of a detail of a portion of the therapy delivery system of FIG. 3.

Referring to FIGS. 3, 4 and 5, another illustrative embodiment of portions of a system 300 for the removal of fluids from the interstitial and intracellular spaces of a patient is presented. The system 300 includes a non-adherent drape 302, which may be formed from any non-adherent film material that helps prevent tissue from adhering to the non-adherent drape 302. In one illustrative embodiment, the non-adherent drape 302 is formed from a breathable polyurethane film. The non-adherent drape 302 is formed with a plurality of fenestrations 304, which may take any shape. In this embodiment, two subsystems may be coupled to or otherwise associated with the non-adherent drape 302: a fluid removal subsystem 306 and an open-cavity, reduced-pressure subsystem 308.

The open-cavity, reduced-pressure subsystem 308 includes a central connection member 310 to which a plurality of encapsulated leg members 312 are fluidly coupled and may also be physically coupled. The central connection member 310 is also encapsulated, except at leg coupling areas 314, which allow fluid communication with the plurality of encapsulated leg members 312. The central connection member 310 has apertures or fenestrations that allow fluid communication with a manifold, e.g., manifold 222 in FIG. 2A, which is in fluid communication with a reduced-pressure source (e.g., reduced-pressure source 232 in FIG. 2A). Each encapsulated leg member 312 may be formed with a plurality of defined leg modules, such as the leg modules 316. Adjacent leg modules 316 are fluidly coupled, but have a manipulation zone 318 between the leg modules 316.

The manipulation zones 318 enhance flexibility and help the plurality of encapsulated leg members 312 to be readily positioned within the body cavity. The manipulation zones 318 also provide a convenient and easy location for the healthcare provider to cut the non-adherent drape 302 and the plurality of encapsulated leg members 312 to size the system 300 for use in a particular patient's body cavity. To further facilitate sizing, visual indicia 320 may be printed or placed on the non-adherent drape 302 to show where the non-adherent drape 302 might be cut. The cut lines, or visual indicia, may run through the manipulation zones 318. As with the subsystem 201 in FIGS. 2A-2D, the encapsulated leg members 312 are each formed with fenestrations that help pull fluids into a leg manifold member, which allows flow toward the central connection member 310.

Turning now to the fluid removal subsystem 306, in this illustrative embodiment, the fluid removal subsystem 306 is associated with the plurality of encapsulated leg members 312. A treatment-fluid delivery bus 324 is positioned on the central connection member 310, but may also be within the central connection member 310 as was shown in FIG. 2A or at a remote site. A plurality of inbound conduits 326 are fluidly coupled to the treatment-fluid delivery bus 324. The treatment-fluid delivery bus 324 is part of a treatment-fluid delivery unit that is operable to deliver a flow of treatment fluid as suggested by arrows to the plurality of inbound conduits 326. The treatment-fluid delivery bus 324 has a treatment-fluid delivery bus port 325 that allows for the treatment fluid to be delivered from a site external to the patient to the treatment-fluid delivery bus 324. The inbound conduits 326 are shown running along side each of the plurality of encapsulated leg members 312.

Referring primarily to FIG. 5, each of the inbound conduits 326 has one or more first couplers 328 that are coordinated with the manipulation zones 318 of the corresponding encapsulated leg member 312 to provide a means for the inbound conduits 326 to be shortened in a coordinated manner with the sizing of the non-adherent drape 302. The first couplers 328 can take numerous shapes and functions to allow the inbound conduit 326 to be uncoupled and to seal off a distal end of the remaining portion of the inbound conduit 326 so that the treatment fluid does not flow into the body cavity. This will be described further below.

Referring again primarily to FIG. 3, a treatment-fluid collecting bus 330 is associated with the central connection member 310. The treatment-fluid collecting bus 330 is formed with a treatment-fluid collecting bus port 332. A plurality of outbound conduits 334 are fluidly coupled to the treatment-fluid collecting bus 330. The treatment-fluid collecting bus port 332 provides a location for coupling to a removal conduit (not shown) for removal of treatment fluid and recruited fluids to a place external to the body cavity. The treatment-fluid collecting bus 330 is part of a treatment-fluid collecting unit that is operable to receive the treatment fluid and the recruited fluid and to remove the fluids to where the fluids may be analyzed with a recruited-fluid determination unit in order to determine the volume of fluid recruited from the patient as well as other parameters as previously discussed.

The plurality of outbound conduits 334 are fluidly coupled, and also may be physically coupled, to the treatment-fluid collecting bus 330. The outbound conduits 334 are run along side each of the encapsulated leg members 312. Each of the outbound conduits 334 may be provided with at least one coupler, e.g., second coupler 336, proximate each of the manipulation zones 318. The second couplers 336 allow the outbound conduits 334 to be adjusted, e.g., uncoupled, in a coordinated manner with the sizes of drape 302. When uncoupled, the second couplers 336 will provide a seal at the distal end of the remaining portion of the outbound conduit 334.

Referring in particular to FIG. 4, a leg module 316 on an encapsulated leg member 312 is presented. The inbound conduit 326 may be fluidly coupled to the outbound conduit 334 by a plurality of tributary conduits 338. The tributary conduits 338 extend into the leg module 316 and may further include an area member 340, which may be a conduit. The tributary conduits 338 and the area member 340 allow for increased surface area, which provides for increased fluid interaction between the treatment fluid and tissue and fluidly connects the conduits 326 and 334. The surface area can be adjusted as a parameter of subsystem 306.

Referring again primarily to FIG. 5, three leg modules 316 are shown along with the two manipulation zones 318 between them. In this view, the inbound conduit 326 may be seen along with two of the first couplers 328 on the inbound conduit 326. In this view, the inbound conduit 326 is shown with a first portion 342 having a proximal end 344 and a distal end 346, a second portion 348 with a proximal end 350 and a distal end 352, and a third portion 354 with a proximal end 356 and a distal end 358. If the healthcare provider desires to size the encapsulated leg member 312 at the most outboard manipulation zone 318, the healthcare provider will cut the manipulation zone 318 after uncoupling the first couplers 328 located at that manipulation zone 318. Thus, the third portion 354 of the inbound conduit 326 would be pulled from the second portion 348 until the third portion 354 is removed. Upon removal, the distal end 352 of the second portion 348 is sealed. In the embodiment shown, the distal end 352 is automatically by the collapsing of the distal end portion 352 to form a closed seal. In an analogous fashion, the first couplers 328 between the first portion 342 and the second portion 348 may be uncoupled. If the inbound conduit 326 is formed as a single integral unit, the inbound conduit 326 may simply be cut and sealed, such as by a cauterizing knife or by any other technique such that the treatment fluid does not flow into the body cavity.

Figure 6:
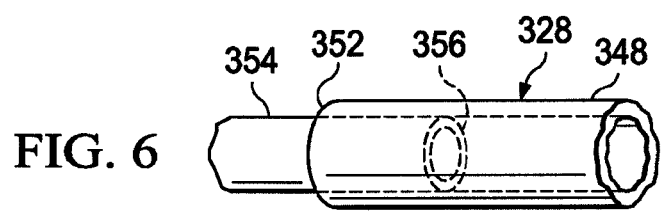
FIG. 6 is a schematic, perspective view of an illustrative embodiment of a coupling device, which is shown in the coupled position and with a portion shown with hidden lines, for use with a therapy delivery system.
Figure 7:
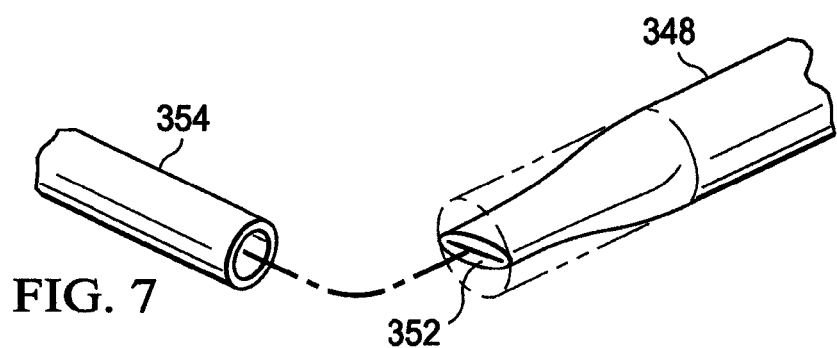
FIG. 7 is a schematic, perspective view of the coupling device of FIG. 6, but now shown in the uncoupled position.

Referring now to FIGS. 6 and 7, an illustrative embodiment of a coupler, such as the first coupler 328 in FIG. 5, is presented. The first couplers 328 may be, for example, the most outboard coupler 328 in FIG. 5 between the second portion 348 and the third portion 354 of the inbound conduit 326. In this illustrative embodiment, the distal end 352 of the second portion 348 has a preformed bias to close but is being held open by the proximal end 356 of the third portion 354. Thus, when the third portion 354 is pulled and removed from within the second portion 348, as is shown in FIG. 7, the distal end 352 collapses to form a seal.

Figure 8A:
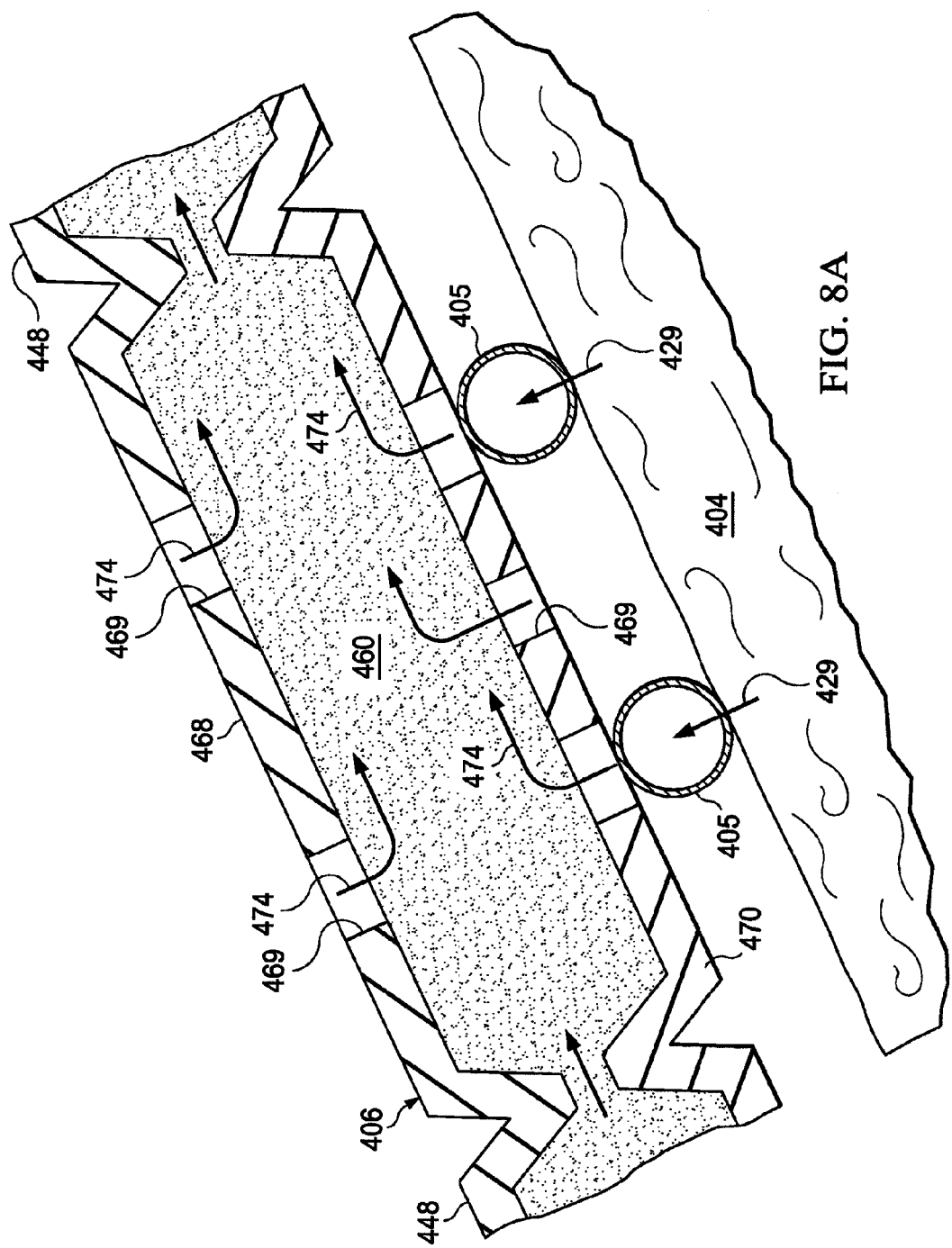
FIG. 8A is a schematic, longitudinal cross section of an encapsulated leg member and nearby components forming a portion of an illustrative embodiment of a therapy delivery system.
Figure 8B:
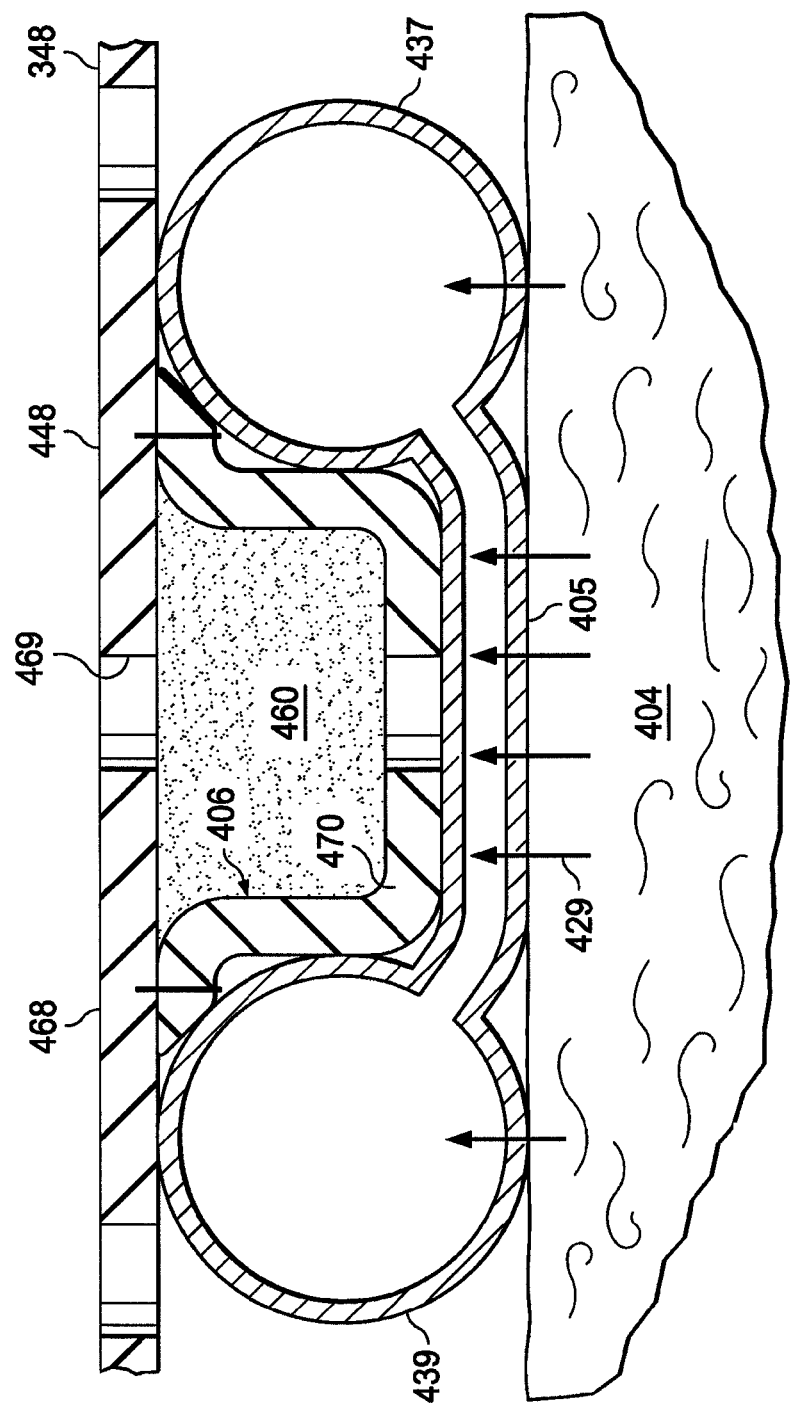
FIG. 8B is a schematic, lateral cross section of the encapsulated leg member and nearby components of the system of FIG. 8A.

Referring now to FIGS. 8A and 8B, one alternative approach to an illustrative fluid removal system is presented. The system is analogous to the system 200 of FIG. 2, but in this embodiment, the tributary conduits 405, which are part of a conduit interface, are placed on an external surface—in this case on an exterior portion of the second leg encapsulating member 470. The tributary conduits 405 may be secured to the exterior of the second leg encapsulating member 470 using any known technique such as those previously given. In this instance, the first leg encapsulating member 468 is part of a non-adherent drape 448. Apertures, or fenestrations 469, allow the flow of fluids into the leg manifold member 460 as suggested by arrows 474. The tributary conduits 405 are placed directly in contact with the tissue site 404. Externally placed the tributary conduits 405 may provide better flow from the intracellular and interstitial spaces to the tributary conduits 405 as suggested by arrows 429. As shown in FIG. 8B, the non-adherent drape 448 may be on top (for the orientation shown) of the inbound conduit 437 and the outbound conduit 439.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A fluid removal system for removing a fluid from a tissue site, comprising:
    a semi-permeable inbound conduit for placement proximate to the tissue site;
    a treatment-fluid delivery unit adapted to be fluidly coupled to the inbound conduit for delivering a treatment fluid to the inbound conduit;
    a semi-permeable outbound conduit for placement proximate to the tissue site, the outbound conduit fluidly coupled to the inbound conduit;
    a treatment-fluid collector adapted to be fluidly coupled to the outbound conduit for receiving the treatment fluid and a recruited fluid from the tissue site; and
    a conduit interface for coupling the inbound conduit and the outbound conduit, the conduit interface comprising a plurality of tributary conduits sized for a patient's abdominal cavity.

2. The system for removing the fluid from the tissue site of claim 1, further comprising a recruited-fluid determination unit coupled to the treatment-fluid collector for determining a volume of the recruited fluid.

3. The system for removing the fluid from the tissue site of claim 1, wherein the treatment fluid is disposed within the inbound conduit and the outbound conduit, wherein the treatment fluid is selected from the group consisting of a hypertonic saline solution, a CaCl2 solution, a KCl solution, a NaCl solution, a Dextran solution and a dry gas.

4. The system for removing the fluid from the tissue site of claim 1, further comprising:
    a volume transducer for developing a signal indicative of a volume of the treatment fluid and the recruited fluid; and
    a treatment controller, the treatment controller comprising:
        a microprocessor,
        a memory device associated with the microprocessor,
        an input device associated with the microprocessor for receiving input signals,
        the volume transducer coupled to the input device,
        an output means associated with the microprocessor for delivering output signals, and
        wherein the microprocessor and the memory device are operable to receive an input signal from the volume transducer and to determine a recruited-fluid volume, and to develop a control signal to deliver to the output means whereby the treatment-fluid delivery unit may be controlled in response to the control signal.

5. The system for removing the fluid from the tissue site of claim 4 wherein the microprocessor and the memory device are further operable to develop a control signal to adjust a flow rate in the treatment-fluid delivery unit.

6. The system for removing the fluid from the tissue site of claim 4 wherein the treatment-fluid delivery unit further comprises a heating element and wherein the system further comprises an inbound conduit temperature transducer coupled to the treatment controller and wherein the treatment controller is further operable to receive an input signal from the temperature transducer and to develop a control signal for delivery to the treatment-fluid delivery unit to adjust the heating element.

7. The system for removing the fluid from the tissue site of claim 1, wherein the tributary conduits are sized and provided in a quantity to provide a desired surface area.

8. The system for removing the fluid from the tissue site of claim 1 wherein the inbound conduit comprises a first portion having a distal end and a proximal end, and a second portion having a distal end and a proximal end, wherein the distal end of the first portion of the inbound conduit and the proximal end of the second portion of the inbound conduit are coupled by a first coupler.

9. The system for removing the fluid from the tissue site of claim 8, wherein the outbound conduit comprises a first portion having a distal end and a proximal end, and a second portion having a distal end and a proximal end, wherein the distal end of the first portion of the outbound conduit and the proximal end of the second portion of the outbound conduit are coupled by a second coupler.

10. The system for removing the fluid from the tissue site of claim 1 further comprising an open-cavity, reduced-pressure subsystem for removing fluids from a body cavity of the patient.

11. The system for removing the fluid from the tissue site of claim 10 wherein the open-cavity, reduced-pressure subsystem comprises:
    a treatment device comprising:
        a fenestrated non-adherent drape,
        a plurality of encapsulated leg members coupled to the non-adherent drape, each having an interior portion with a leg manifold member and formed with fenestrations operable to allow fluid flow into the interior portion, and
        a central connection member fluidly coupled to the plurality of encapsulated leg members, the central connection member having a first side and a second, patient-facing side;
    a manifold for disposing proximate the first side of the central connection member and operable to manifold reduced pressure to the central connection member;
    a sealing member for disposing on a portion of the patient's epidermis and operable to form a pneumatic seal over the body cavity;
    a reduced-pressure delivery conduit; and
    a reduced-pressure interface for coupling to the sealing member and operable to fluidly couple the reduced-pressure delivery conduit to the manifold.

12. The system for removing the fluid from the tissue site of claim 11 wherein the central connection member has a connection manifold member and wherein each leg manifold member is in fluid communication with the connection manifold member.

13. The system for removing the fluid from the tissue site of claim 11 wherein the outbound conduit and the inbound conduit are coupled to at least one of the plurality of encapsulated leg members.

14. The system for removing the fluid from the tissue site of claim 11, further comprising the treatment fluid disposed within the inbound conduit and the outbound conduit, wherein the treatment fluid is selected from the group consisting of a hypertonic saline solution, a CaCl2 solution, a KCl solution, a NaCl solution, a Dextran solution and a dry gas.

15. The system for removing the fluid from the tissue site of claim 11, further comprising a volume transducer for developing a signal indicative of a volume of the treatment fluid and the recruited fluid, and a treatment controller, the treatment controller comprising:
    a microprocessor;
    a memory device associated with the microprocessor;
    an input device associated with the microprocessor for receiving input signals;
    the volume transducer coupled to the input device;
    an output device associated with the microprocessor for delivering output signals; and
    wherein the microprocessor and the memory device are operable to receive an input signal from the volume transducer and to determine a recruited-fluid volume, and to develop a control signal to deliver to the output device whereby the treatment-fluid delivery unit may be controlled in response to the control signal.

16. The system for removing the fluid from the tissue site of claim 15 wherein the microprocessor and the memory device are further operable to develop a control signal to adjust a flow rate in the treatment-fluid delivery unit.

17. The system for removing the fluid from the tissue site of claim 16 wherein the treatment-fluid delivery unit further comprises a heating element and wherein the system further comprises an inbound conduit temperature transducer coupled to the treatment controller and wherein the treatment controller is further operable to receive an input signal from the temperature transducer and to develop a control signal for delivery to the treatment-fluid delivery unit to adjust the heating element.

18. The system for removing the fluid from the tissue site of claim 11 wherein each encapsulated leg member of the plurality of encapsulated leg members comprises:
    a fenestrated first leg encapsulating member;
    a fenestrated second leg encapsulating member;
    wherein the leg manifold member has a first side, a second side, a first lateral edge, and a second lateral edge;
    wherein the first leg encapsulating member is disposed proximate the first side of the leg manifold member, the second leg encapsulating member is disposed proximate the second side of the leg manifold member, and the first leg encapsulating member and the second leg encapsulating member are coupled proximate the first lateral edge and the second lateral edge of the leg manifold member to form the first encapsulated leg member.

19. A system for removing a fluid from a tissue site, comprising:
    a semi-permeable inbound conduit for placement proximate to the tissue site;
    a treatment-fluid delivery unit adapted to be fluidly coupled to the inbound conduit for delivering a treatment fluid to the inbound conduit;
    a semi-permeable outbound conduit for placement proximate to the tissue site, the outbound conduit fluidly coupled to the inbound conduit;
    a treatment-fluid collector adapted to be fluidly coupled to the outbound conduit for receiving the treatment fluid and a recruited fluid from the tissue site; and
    a conduit interface for coupling the inbound conduit and the outbound conduit, the conduit interface comprising a plurality of tributary conduits sized for a patient's abdominal cavity;
    wherein the treatment fluid is hyperosmotic with respect to the tissue site and comprises a dry gas.

20. The system of claim 19, further comprising a recruited-fluid determination unit coupled to the treatment-fluid collector for determining a volume of the recruited fluid.

21. The system of claim 19, further comprising:
    a volume transducer for developing a signal indicative of a volume of the treatment fluid and the recruited fluid; and
    a treatment controller, the treatment controller comprising:
        a microprocessor,
        a memory device associated with the microprocessor,
        an input device associated with the microprocessor for receiving input signals,
        the volume transducer coupled to the input device,
        an output means associated with the microprocessor for delivering output signals, and wherein the microprocessor and the memory device are operable to receive an input signal from the volume transducer and to determine a recruited-fluid volume, and to develop a control signal to deliver to the output means whereby the treatment-fluid delivery unit may be controlled in response to the control signal.

22. The system of claim 21, wherein the microprocessor and the memory device are further operable to develop a control signal to adjust a flow rate in the treatment-fluid delivery unit.

23. The system of claim 21, wherein the treatment-fluid delivery unit further comprises a heating element and wherein the system further comprises an inbound conduit temperature transducer coupled to the treatment controller and wherein the treatment controller is further operable to receive an input signal from the temperature transducer and to develop a control signal for delivery to the treatment-fluid delivery unit to adjust the heating element.

24. The system of claim 19, wherein the inbound conduit comprises a first portion having a distal end and a proximal end, and a second portion having a distal end and a proximal end, wherein the distal end of the first portion of the inbound conduit and the proximal end of the second portion of the inbound conduit are coupled by a first coupler.

25. The system of claim 24, wherein the outbound conduit comprises a first portion having a distal end and a proximal end, and a second portion having a distal end and a proximal end, wherein the distal end of the first portion of the outbound conduit and the proximal end of the second portion of the outbound conduit are coupled by a second coupler.

26. The system of claim 19, further comprising an open-cavity, reduced-pressure subsystem for removing fluids from a body cavity of the patient.

27. The system of claim 26, wherein the open-cavity, reduced-pressure subsystem comprises:
  a treatment device comprising:
    a fenestrated non-adherent drape,
    a plurality of encapsulated leg members coupled to the non-adherent drape, each having an interior portion with a leg manifold member and formed with fenestrations operable to allow fluid flow into the interior portion, and
    a central connection member fluidly coupled to the plurality of encapsulated leg members, the central connection member having a first side and a second, patient-facing side;
  a manifold for disposing proximate the first side of the central connection member and operable to manifold reduced pressure to the central connection member;
  a sealing member for disposing on a portion of the patient's epidermis and operable to form a pneumatic seal over the body cavity;
  a reduced-pressure delivery conduit; and
  a reduced-pressure interface for coupling to the sealing member and operable to fluidly couple the reduced-pressure delivery conduit to the manifold.

28. The system of claim 27, wherein the central connection member has a connection manifold member and wherein each leg manifold member is in fluid communication with the connection manifold member.

29. The system of claim 27, wherein the outbound conduit and the inbound conduit are coupled to at least one of the plurality of encapsulated leg members.

30. The system of claim 27, wherein each encapsulated leg member of the plurality of encapsulated leg members comprises:
  a fenestrated first leg encapsulating member;
  a fenestrated second leg encapsulating member;
  wherein the leg manifold member has a first side, a second side, a first lateral edge, and a second lateral edge;
  wherein the first leg encapsulating member is disposed proximate the first side of the leg manifold member, the second leg encapsulating member is disposed proximate the second side of the leg manifold member, and the first leg encapsulating member and the second leg encapsulating member are coupled proximate the first lateral edge and the second lateral edge of the leg manifold member to form the first encapsulated leg member.

* * * * *